United States Patent [19]
Truckai

[11] Patent Number: 5,397,304
[45] Date of Patent: * Mar. 14, 1995

[54] SHAPABLE HANDLE FOR STEERABLE ELECTRODE CATHETER

[75] Inventor: Csaba Truckai, Sunnyvale, Calif.

[73] Assignee: Medtronic Cardiorhythm, San Jose, Calif.

[*] Notice: The portion of the term of this patent subsequent to Jun. 7, 2011 has been disclaimed.

[21] Appl. No.: 85,220

[22] Filed: Jun. 29, 1993

Related U.S. Application Data

[63] Continuation-in-part of Ser. No. 867,241, Apr. 10, 1992, abandoned.

[51] Int. Cl.$^6$ .............................................. A61M 37/00
[52] U.S. Cl. ...................................................... 604/95
[58] Field of Search ...................... 604/95, 281, 282; 128/772, 657, 642, 786, 790, 780; 607/122

[56] References Cited

U.S. PATENT DOCUMENTS

| | | |
|---|---|---|
| 3,470,876 | 10/1969 | Barchilon . |
| 3,547,103 | 12/1970 | Cook . |
| 3,552,384 | 1/1971 | Pierie et al. . |
| 3,605,725 | 9/1971 | Bentov . |
| 3,625,200 | 12/1971 | Muller . |
| 3,773,034 | 11/1973 | Burns et al. . |
| 4,277,168 | 7/1981 | Oku . |
| 4,685,457 | 8/1987 | Donenfeld . |
| 4,723,936 | 2/1988 | Buchbinder et al. . |
| 4,753,223 | 6/1988 | Bremer . |
| 4,769,006 | 9/1988 | Papantonakos . |
| 4,826,087 | 5/1989 | Chinery . |
| 4,838,859 | 6/1989 | Strassman . |
| 4,874,371 | 10/1989 | Comben et al. . |
| 4,886,067 | 12/1989 | Palermo . |
| 4,944,727 | 7/1990 | McCoy . |
| 4,960,134 | 10/1990 | Webster, Jr. . |
| 4,998,916 | 3/1991 | Hammerslag et al. . |
| 5,055,109 | 10/1991 | Gould et al. . |
| 5,060,660 | 10/1991 | Gambale et al. . |
| 5,106,381 | 4/1992 | Chikama . |
| 5,125,896 | 6/1992 | Hojeibane . |
| 5,176,126 | 1/1993 | Chikama . |

FOREIGN PATENT DOCUMENTS

| | | |
|---|---|---|
| 476807 | 3/1992 | European Pat. Off. . |
| 1213571 | 3/1966 | Germany . |
| 90734 | 11/1937 | Sweden . |
| 882477 | 11/1961 | United Kingdom . |
| 1046478 | 10/1966 | United Kingdom . |
| WO91/11213 | 8/1991 | WIPO . |

Primary Examiner—C. Fred Rosenbaum
Assistant Examiner—Manuel A. Mendez
Attorney, Agent, or Firm—Townsend & Townsend Khourie & Crew

[57] ABSTRACT

A steerable catheter suitable for radiofrequency ablation of cardiac tissue comprises a catheter shaft with a deflectable tip at the distal end of the shaft. The tip is deflected by means of a shapable handle coupled to pull wires fastened to the distal end of the deflectable tip. A core wire extends from the handle to the distal tip, providing fine positioning of the deflectable tip by applying torque through the core wire to the tip. A spring tube is further provided in the deflectable tip for improved torque transmission and kink-resistance. The catheter has an electrode at the distal end of the deflectable tip for positioning at a target site and applying RF power to accomplish ablation.

42 Claims, 7 Drawing Sheets

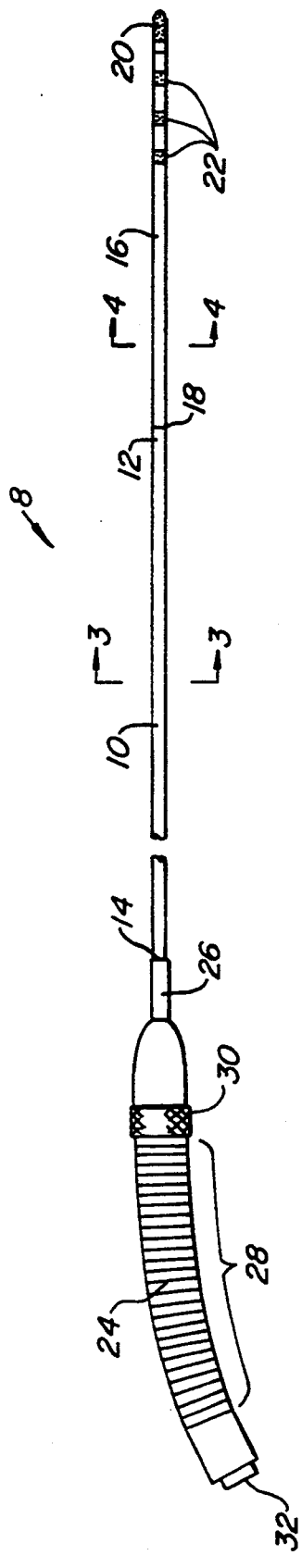
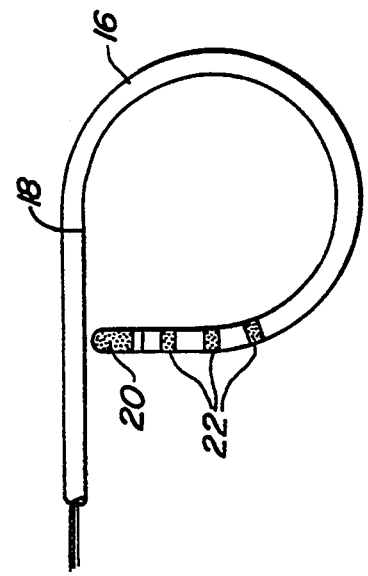
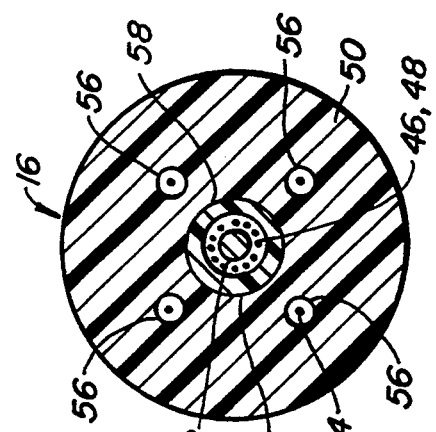
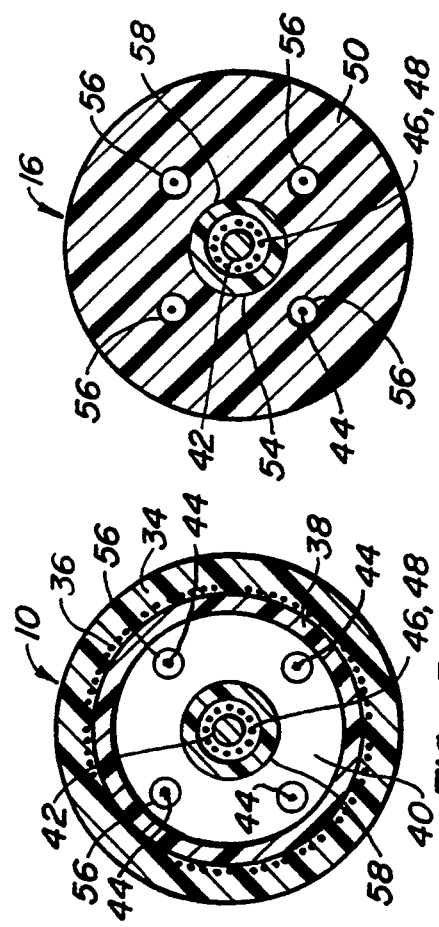

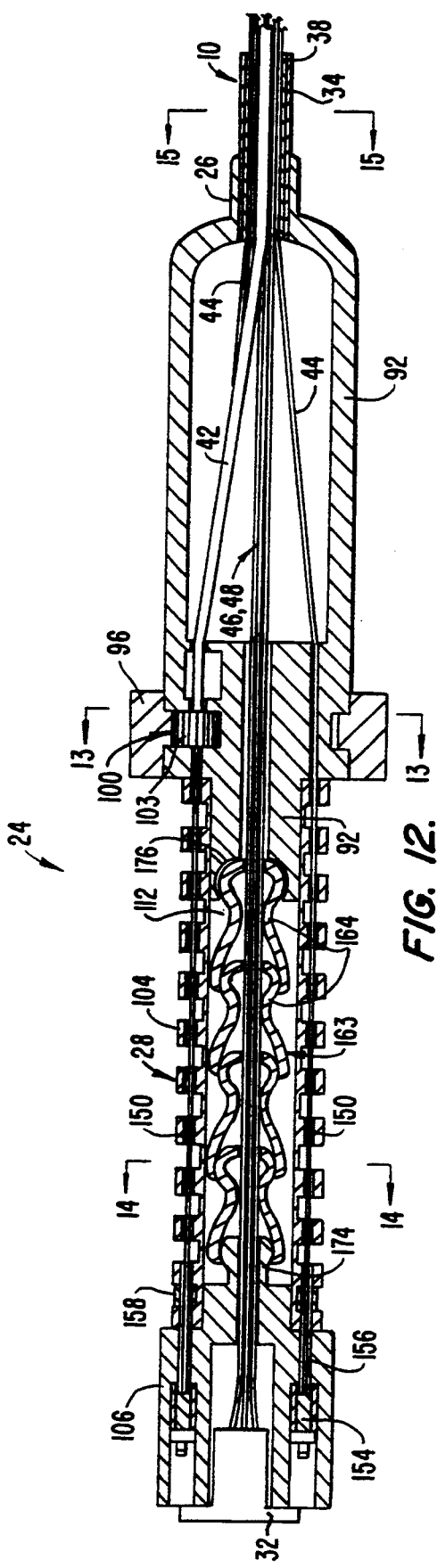

SHAPABLE HANDLE FOR STEERABLE ELECTRODE CATHETER

CROSS-REFERENCE TO RELATED APPLICATIONS

The present application is a continuation-in-part of application Ser. No. 07/867,241, now abandoned, filed Apr. 10, 1992, the complete disclosure of which is incorporated herein by reference.

The present application is further related to co-pending application Ser. Nos. 07/866,763, now abandoned (Atty. Docket 14875-1), 07/866,383 (Atty. Docket 14875-2), now U.S. Pat. No. 5,318,525 and 07/866,683 (Atty. Docket 14875-8) application Pending, all filed on Apr. 10, 1993. The disclosures of all of these co-pending applications are incorporated herein by reference.

BACKGROUND OF THE INVENTION

The present invention relates generally to the field of electrophysiology. More particularly, this invention relates to methods and apparatus for treating cardiac arrhythmias.

Symptoms of abnormal heart rhythm are generally referred to as cardiac arrhythmias, with an abnormally slow rhythm being classified as a bradycardia and an abnormally rapid rhythm being referred to as a tachycardia. The present invention is concerned with the treatment of tachycardias which are frequently caused by the presence of an "arrhythmogenic site" or "accessory atrioventricular pathway" close to the inner surface of one of the chambers of the heart. The heart includes a number of normal pathways which are responsible for the propagation of signals necessary for normal electrical mechanical function. The presence of arrhythmogenic sites or accessory pathways can bypass or short circuit the normal pathways, potentially resulting in very rapid heart contractions, referred to as tachycardias. Tachycardias may be defined as ventricular tachycardias (VT's) and supraventricular tachycardias (SVT's). VT's originate in the left or right ventricle and are typically caused by arrhythmogenic sites associated with a prior myocardial infarction. SVT's originate in the atria and are typically caused by an accessory pathway.

Treatment of both ventricular and supraventricular tachycardias may be accomplished by a variety of approaches, including drugs, surgery, implantable pacemakers/defibrillators, and catheter ablation. While drugs may be the treatment of choice for many patients, they only mask the symptoms and do not cure the underlying cause. Implantable devices only correct the arrhythmia after it occurs. Surgical and catheter-based treatments, in contrast, will actually cure the problem, usually by ablating the abnormal arrhythmogenic tissue or accessory pathway responsible for the tachycardia. The catheter-based treatments rely on the application of various destructive energy sources to the target tissue, including direct current electrical energy, radiofrequency electrical energy, laser energy, and the like.

Of particular interest to the present invention are radiofrequency (RF) ablation protocols which have proven to be highly effective in tachycardia treatment while exposing the patient to minimum side effects and risks. Radiofrequency catheter ablation is generally performed after an initial mapping procedure where the locations of the arrhythmogenic sites and accessory pathways are determined. After mapping, a catheter having a suitable electrode is introduced to the appropriate heart chamber and manipulated so that the electrode lies proximate the target tissue. Radiofrequency energy is then applied through the electrode to the cardiac tissue in order to ablate a region of the tissue which forms part of arrhythmogenic site or the accessory pathway. By successfully destroying that tissue, the abnormal signalling patterns responsible for the tachycardia cannot be sustained. A method and system for performing RF ablation by controlling temperature at the ablation site is described in co-pending application Ser. No. 07/866,683, entitled "Method and System for Radiofrequency Ablation of Cardiac Tissue," Attorney Docket No. 14875-8, the full disclosure of which is hereby incorporated herein by reference.

Catheters utilized in radiofrequency ablation are inserted into a major vein or artery, usually in the neck or groin area, and guided into the chambers of the heart by appropriate manipulation through the vein or artery. The tip of the catheter must be manipulable by the user from the proximal end of the catheter, so that the distal electrode can be positioned against the tissue region to be ablated. The catheter must have a great deal of flexibility in order to follow the pathway of the major blood vessels into the heart, and the catheter must permit user manipulation of the tip even when the catheter is in a curved and twisted configuration. Because of the high degree of precision required for proper positioning of the tip electrode, the catheter must be manipulable with a high degree of sensitivity and controllability. In addition, the distal portion of the catheter must be sufficiently resilient in order to be positioned against the wall of the ventricle and maintained in a position during ablation without being displaced by the movement of the beating heart. Along with the steerability, flexibility and resiliency, the catheter must have a sufficient degree of torsional stiffness to permit user manipulation from the proximal end.

Steerable catheters are known for use in various medical procedures. See, for example, U.S. Pat. No. 4,998,916 to Hammerslag, U.S. Pat. No. 4,944,727 to McCoy, U.S. Pat. No. 4,838,859 to Strassmann, U.S. Pat. No. 4,826,087 to Chinery, U.S. Pat. No. 4,753,223 to Bremer, U.S. Pat. No. 4,685,457 to Donenfeld, U.S. Pat. No. 3,605,725 to Bentov, U.S. Pat. No. 3,470,876 to Barchilon and U.S. Pat. No. 4,960,134 to Webster, Jr. Typically, such catheters employ a plurality of steering wires, usually three or four, extending from a steering mechanism at the proximal end of the catheter to an anchor point at the distal end of the catheter. By tensioning certain of the steering wires using the control mechanism, the tip of the catheter can be manipulated in a desired direction. Known steering mechanisms include joy sticks, e.g. U.S. Pat. Nos. 4,960,134, 4,944,727, 4,838,859, 4,826,087, and 3,605,725, movable plates, e.g. U.S. Pat. No. 4,998,916, and trigger arms, e.g. U.S. Pat. No. 3,470,876.

In addition to being steerable in the lateral direction, further positioning of known catheters is accomplished by rotating the catheter as a whole about its longitudinal axis, typically by turning or twisting the proximal end of the catheter. This exerts a torque along the length of the catheter which is translated into a rotational motion at the distal end, allowing a laterally deflected distal tip to be rotated.

While radiofrequency ablation using existing catheters has had promising results, such catheters suffer from certain disadvantages. In particular, the steering mechanisms utilized in known catheters have proven to be awkward and ill-suited to the delicate and precise positioning required in ablation procedures. Joysticks and other known mechanisms frequently lack any obvious correspondence between the deflection of the mechanism and the resulting deflection produced at the distal tip of the catheter. Moreover, previous joysticks tend to be complex and are often costly and difficult to manufacture in volume. Further, known mechanisms usually have an additional actuator member as an appendage of the catheter handle, requiring the user to simultaneously maintain a grip on the catheter while actuating the steering mechanism, an action which frequently requires the use of more than one hand. In addition, joysticks and other manipulators are frequently unable to apply the amount of force required to manipulate a pull wire system, in catheters or other instruments.

For these and other reasons, a steerable catheter suitable for radiofrequency ablation is desired which is steerable from its proximal end in a controllable and convenient manner. The catheter should have a steering mechanism for high-precision positioning of the catheter's distal end which is simplified and intuitive in operation. Preferably, the direction and magnitude of deflection produced at the distal end of the catheter will correlate with the direction and magnitude of movement of the steering mechanism. It would be further desirable for the steering mechanism to be integrated into the handle of the catheter to facilitate simultaneously holding and steering mechanism to be integrated into the handle of the catheter to facilitate simultaneously holding and steering the catheter with one hand. Such designs should also facilitate simultaneous tip deflection and rotation of the catheter (by applying torque to the proximal end). In addition, the steering mechanisms or "manipulators" should be able to apply relatively large manipulation forces and be adaptable to function with any type of instrument having a pull wire deflection system, such as endoscopes and industrial equipment.

SUMMARY OF THE INVENTION

The present invention provides an improved manipulator, in particular a shapable handle, for use with a steerable catheter in, for example, radiofrequency ablation, where the shapable handle is disposed at the proximal end of the catheter for steering the deflectable tip of the catheter. The shapable handle will further be suitable for use with other equipment and instruments which rely on a pull wire or push rod system for tip deflection.

In one embodiment, the shapable handle comprises a deformable body capable of being attached at its distal end to the proximal end of the catheter, with a proximal portion of the body attached to a linkage coupled to the deflectable tip of the catheter, wherein deforming the body about a first transverse axis deflects the deflectable tip about a second parallel or non-parallel transverse axis. Preferably, the deformable body comprises convoluted tubing, and is substantially non-resilient so as to retain its shape after being deflected. Usually, the linkage from the deflectable tip comprises at least one pair of pull wires, the distal ends of the pull wires being coupled to radially offset locations at the distal end of the deflectable tip, and the proximal ends of the pull wires being attached to radially offset locations at the proximal end of the deformable body, whereby deforming the body about the first transverse axis tensions at least a first of the pull wires. The pull wires are preferably disposed in radially offset passages extending from the distal end to the proximal end of the body. In addition, the deformable body may include means for maintaining the handle body in a laterally deflected shape. In a preferred embodiment, the means for maintaining shape comprises a spine having a plurality of linked elements pivotally coupled to one another.

In a further embodiment, the shapable handle includes means for torquing the deflectable tip about a longitudinal axis of the catheter shaft without rotating the handle of the catheter. Usually, the means for torquing comprises a core wire extending from the deflectable tip to the handle, and means mounted on the handle for applying torque to a proximal end of the core wire, whereby the torque applied is transmitted to the distal end of the deflectable tip. The means for applying torque may comprise a torquer ring rotatably mounted to the handle, and means for coupling the torquer ring to the proximal end of the core wire. The coupling means may comprise a knurled ring for frictional engagement with an inner surface of the torquer ring, or alternatively, a pinion gear having a plurality of gear teeth for engaging drive teeth of complementary configuration on the inner surface of the torquer ring.

In addition, the handle preferably includes a connector to which lead wires from the electrodes at the distal end of the catheter are coupled. The connector will typically be suitable for connection to an RF generator, as well as to mapping or diagnostic equipment.

The steerable catheter of the present invention has several important advantages over known catheters. The catheter of the invention is steerable from its proximal end with sensitivity and precision. The shapable handle provides a steering mechanism which is much simplified in operation over existing mechanisms. The shapable handle provides an obvious and logical correlation between the shape of the handle and the resulting deflection produced in the tip of the catheter. The shapable handle further provides means for holding, steering and rotating the catheter in a single member, conveniently operable using a single hand, eliminating the awkwardness of a separate actuator extending from the catheter handle.

The invention and objects and features thereof will be more readily apparent from the following detailed description and appended claims when taken with the drawings.

BRIEF DESCRIPTION OF THE DRAWING

FIG. 1 is a side elevational view of a steerable catheter constructed in accordance with the principles of the present invention.

FIG. 2 is a side elevational view of a distal portion of the catheter of FIG. 1.

FIG. 3 is a transverse cross-sectional view of the catheter body taken along line 3—3 of FIG. 1.

FIG. 4 is a transverse cross-sectional view of the distal portion of the catheter taken along line 4—4 of FIG. 1.

FIG. 12 is a side cross-sectional view of a further embodiment of the shapable handle of the present invention;

FIGS. 13–15 are transverse cross-sectional views through lines 13—13, 14—14, and 15—15, respectively, in the shapable handle of FIG. 12;

FIG. 16 is a perspective view of a linked element in the shapable handle of FIG. 12.

DETAILED DESCRIPTION OF THE ILLUSTRATIVE EMBODIMENTS

Figure 5:
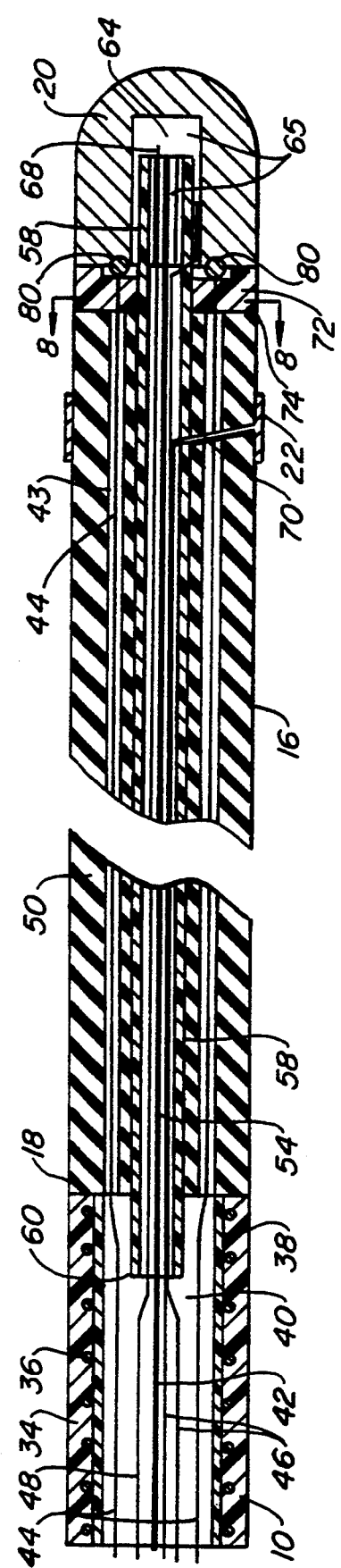
FIG. 5 is a side cross-sectional view of the distal tip of the catheter of FIG. 1.

Referring to FIG. 1, a steerable catheter 8 constructed in accordance with the principles of the present invention comprises a shaft 10 having a distal end 12 and proximal end 14. A tip section 16 is fused at butt joint 18 to distal end 12 of shaft 10. A tip electrode 20 is mounted at the distal end of tip section 16, with band electrodes 22 disposed on tip section 16 proximally of tip electrode 20. A thermocouple (not shown) is located in the distal end of the tip section 16 and in thermal contact with the tip electrode 20. Proximal end 14 of shaft 10 is mounted to handle 24 through strain relief 26. Handle 24 includes a shapable body 28 in a middle portion thereof. A torque ring 30 is disposed about handle 24 distally of shapable body 28, as shown in FIG. 1, or proximally thereof. At the proximal end of handle 24 is electrical connector 32 for connecting tip electrode 20, band electrodes 22 and the thermocouple to RF power, mapping, and/or temperature measuring equipment. Tip section 16, as illustrated in FIG. 2, is flexible and laterally deflectable into various configurations using shapable handle 24. Preferably, tip section 16 can be deflected by at least 270° from the straight, distally-pointing configuration of FIG. 1 (as illustrated in FIG. 2).

Referring now to FIGS. 1, 3 and 5, shaft 10 comprises an outer jacket 34, which may be nylon, urethane or other plastic. Outer jacket 34 surrounds stiffener 36, which usually comprises a stainless steel braid or coil. The stiffener 36 is disposed about a base layer 38, which preferably comprises a tube of polyimide, polyetherimide, or other relatively stiff, high durometer material. The stiffness and torqueability characteristics of the shaft can be varied by varying the type of material used for outer jacket 34, stiffener 36 and base layer 38, as well as by using different geometries for the stiffener 38. For example, the stiffener 36 could be a braid or a coil, where the number of filaments, shape of filaments, coiling or weaving pattern, number of turns, and the like, can be varied individually or in combination to provide a desired stiffness. Preferably, the polyimide or polyetherimide tube of base layer 38 has a thickness in the range from 0.002 in to 0.005 in.

Outer jacket 34, stiffener 36 and base layer 38 define a central lumen 40 extending the length of shaft 10. Disposed in central lumen 40 are a core wire 42, pull wires 44, electrode wires 46 and thermocouple wires 48.

Referring now to FIGS. 1, 4 and 5, tip section 16 comprises tubing 50 of a low durometer flexible plastic, such as Pebax TM, silicone rubber, or other resilient material. Preferably, tip section 16 has a durometer in the range of 30A to 60D. Tubing 50 preferably has at least four lumens extending its length in parallel to its longitudinal axis, that is a central lumen 54 and at least three radially offset lumens 56 (with four being illustrated). Core wire 42 extends through central lumen 54, along with electrode wires 46 and thermocouple wires 48. Pull wires 44 extend from the central lumen 40 of shaft 10 to the radially offset lumens 56 of tip section 16.

A spring tube 58 is also disposed in central lumen 54 of tip section 16, the spring tube 58 fitting snugly against the walls of inner lumen 54 and having a hollow center through which core wire 42, electrode wires 46 and thermocouple wires 48 extend. Spring tube 58 usually comprises a polyimide tube which provides lateral and torsional stiffness as well as kink-resistance to tip section 16. The spring tube 58 could also be a braided or coiled structure, or a composite of multiple layers.

Referring now particularly to FIG. 5, tip section 16 is fixed to shaft 10 at butt joint 18, preferably by heat welding. Central lumen 54 of tip section 16 is of smaller diameter than central lumen 40 of shaft 10, with spring tube 58 extending a distance, typically about 0.5 in., into the central lumen 40 of shaft 10. Such extension serves to limit kinking at or near butt joint 18 when tip section 16 is deflected. A proximal end 60 of the spring tube 58 will extend into central lumen 40, thereby enhancing the stiffness at the transition between the tip section 16 and the remainder of the shaft 10.

Core wire 42, electrode wires 46 and thermocouple wires 48 extend from central lumen 40 of shaft 10 into central lumen 54 of tip section 16 through the center of spring tube 58. At the distal end of tip section 16, spring tube 58 emerges from central lumen 54 into an aperture 64 within tip electrode 20. RF power wire 66 (one of electrode wires 46) is coupled to tip electrode 20. Thermocouple wires 48 terminate in a thermocouple 68 disposed within aperture 64. Preferably, aperture 64 is filled with high temperature adhesive to maintain thermocouple 68 in position. Electrode band wires 70 exit central lumen 54 within spring tube 58 and couple to band electrodes 22. Core wire 42 extends through central lumen 54 into aperture 64 of tip electrode 20.

Figure 8:
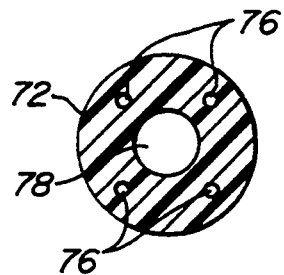
FIG. 8 is a front view of the anchor plate of the catheter of FIG. 1 as viewed along line 8—8 of FIG. 5.

An electrically and thermally insulating anchor plate 72 is bonded to distal end 74 of tubing 50, tip electrode 20 being bonded to the distal side of anchor plate 72. Anchor plate 72, as shown in FIG. 8, has a central passage 78 corresponding to central lumen 54 of tip section 16, and four radially offset apertures 76 through which pull wires 44 pass. Referring again to FIG. 5, pull wires 44 terminate in anchors 80, which usually comprise steel balls formed on or welded to ends of pull wires 44. The anchors 80 are of larger diameter than apertures 76, providing a strong, pivotal connection between pull wires 44 and the distal end of tip section 16. Anchor plate 72 serves several functions. First, it protects the catheter body from thermal damage during ablation, allowing for many RF applications without catheter degradation. Secondly, it provides a strong component to which the pull wires 44 can be attached, without reliance on adhesive. Third, anchor plate 72 provides a means of electrically insulating the pull wires 44 from tip electrode 20, preventing the RF current from traveling back up the catheter to the handle assembly. The anchor plate may be formed from any polymeric or ceramic material having the necessary mechanical strength and electrical and thermal insulating properties. Preferred is the use of polyether ether ketone, available from ICI Americas, Inc., Wilmington, Del., under the tradename Victrex.

Figure 6:
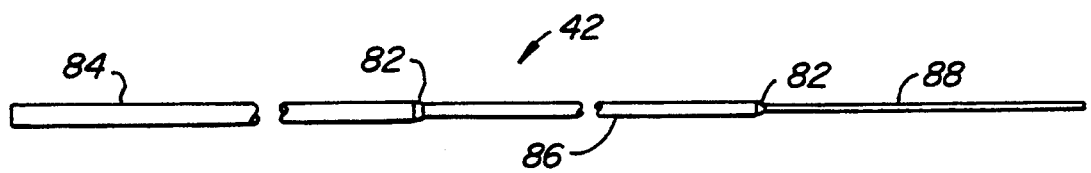
FIG. 6 is a side elevational view of the core wire of the catheter of FIG. 1.
Figure 7:
FIG. 7 is a side elevational view of a pull wire of the catheter of FIG. 1.

Referring now to FIG. 6, core wire 42 is usually stainless steel, and is tapered, typically being ground in three sections of different diameter separated by tapered transition sections 82. Proximal shaft portion 84 has the largest diameter, to provide the greatest stiffness both laterally and torsionally to the proximal portion of shaft 10 of the catheter. Distal shaft section 86 has an intermediate diameter, providing significantly more flexibility than that of the proximal shaft section 84 so as to allow deflection of the corresponding distal portion of shaft 10 of the catheter. Distal portion 88 of core wire 42 is of the smallest diameter, lending the highest degree of flexibility to tip section 16. The graduated diameters of the core wire permit deflection of tip section 16 at a constant or near constant radius. Core wire 42 further provides a structural member continuous from the proximal end to the distal end of the catheter having a significant degree of torsional stiffness. The taper profile of the core wire 42 may of course be varied to obtain any of a variety of tip shapes.

In addition to controlled flexibility, the core wire can provide an alternate means for transmitting torque to the catheter tip. By coupling the core wire to a rotatable ring on the handle of the catheter, as described below, torque can be applied to the distal tip of the catheter without having to rotate the entire handle assembly. The core wire further permits greater controllability and sensitivity in rotational positioning of tip electrode 20 than is afforded by turning the entire handle and catheter assembly.

Usually, pull wires 44 are stainless steel coated with a low friction plastic such as polytetrafluoroethylene (available from DuPont under the tradename Teflon®). Electrode wires 46 are usually nickel for increased tensile strength but could be copper or other electrically conductive metals. Thermocouple wires 48 are usually copper and constantan, respectively.

Figure 9:
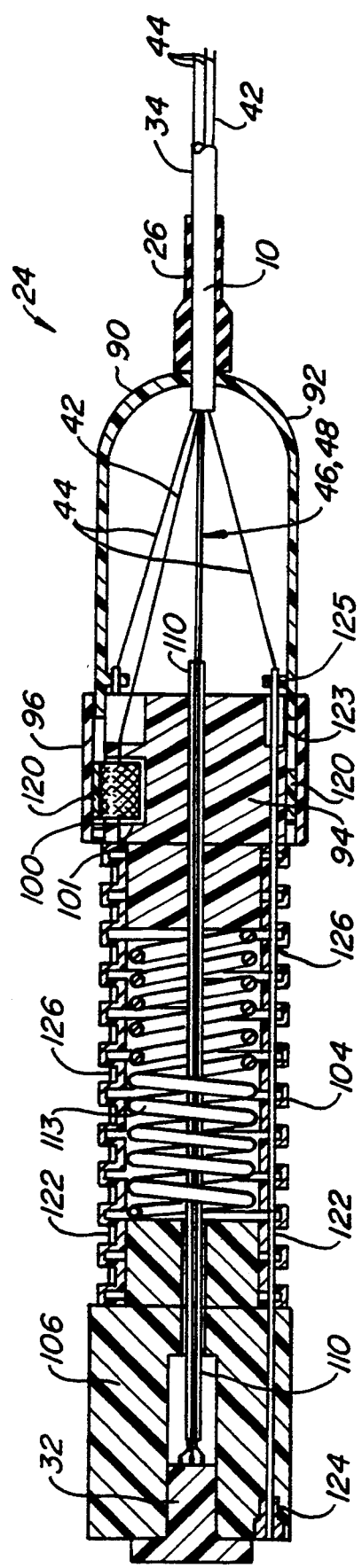
FIG. 9 is a side cross-sectional view of the shapable handle of the catheter of FIG. 1.

Referring now to FIG. 9, the shapable handle 24 of the steerable catheter 8 will now be described. Shaft 10 is mounted to the distal end 90 of handle 24 through strain relief 26. Outer jacket 34 of shaft 10 is fixed to handle 24 by heat or adhesive bonding, or other known means. Handle 24 is comprised of a nose cover 92, a distal frame member 94 adjacent nose cover 92, a torquer ring 96 disposed about a portion of distal frame member 94, an inner ring 100 received in a cavity 101 formed in distal frame member 94, and convoluted tubing 104 extending between the distal frame member 94 and a proximal frame member 106. The convoluted tubing 104 may alternately be formed as a series of stacked disks, a gooseneck structure, or the like. The electrical connector 32 is secured to proximal end of proximal frame member 106. In addition, a bridge member 110, usually a nylon or polyethylene tube, extends between proximal frame member 106 and the distal frame 94 and is bonded at each end by adhesives or other means. Electrode wires 46 and thermocouple wires 48 extend from the connector 36 in proximal frame member 106 through bridge 110 to nose cover 92 and into shaft 10. A spring 113 may be provided in bore 112 for enhancing the hoop strength and axial stiffness of the convoluted tubing 104. Spring 113 may also be a soft malleable material such as copper or brass so as to maintain convoluted tubing 104 in a deflected shape, holding pull wires 44 in tension.

Core wire 42 enters nose cover 92 from shaft 10 and angles radially outward so as to mechanically couple with torquer ring 96. The proximal end of core wire 42 is fixed to inner ring 100, usually being adhesively bonded in a center hole in inner ring 100 or engaged by a set screw (not illustrated) in the inner ring. Inner ring 100 is cylindrical in shape and lies within a cavity 101 of distal frame member 94, such that turning torquer ring 96 rolls inner ring 100. In an exemplary embodiment, the outer surface of inner ring 100 is knurled, and a friction pad 120 is disposed between inner ring 100 and torquer ring 96, for improved contact therebetween. Other mechanisms for applying torque to the proximal end of the core wire 42, of course, would also be available, such as rack and pinion systems where the interior surface of torquer ring 96 would have a gear surface to engage an exterior gear surface of inner ring 100. It would also be possible for inner ring 100 to have a cross-sectional shape other than round, such as oval, in order to transmit a variable force to the core wire 42. Thus, by rotating torquer ring 96, inner ring 100 is rotated, thereby applying a torque to the proximal end of core wire 42, whereby the torque will be transmitted to the distal tip section 16 of the catheter 8.

The relative diameters of inner ring 100 and torquer ring 96 will be selected to provide a particular ratio between ring rotation and wire rotation, usually being between 1:1.5 and 1:8, and preferably about 1:4 (torquer ring:control wire). In this way, a small rotation of the torque ring 96 can cause a greater rotation of the proximal end of core wire 100. The ratio can be varied depending on, for example, the torsional stiffness of the core wire 100 and other variable factors.

Pull wires 44 enter the handle from shaft 10 and angle radially outward so as to pass through tubes 122. Tubes 122 are preferably stainless steel and extend through the distal frame member 94, the passages 126 in convoluted tube member 104 and to anchor points 124 at the proximal end of proximal frame member 106. Preferably, anchor points 124 comprise tensioning screws for adjusting the tension of pull wires 44. To provide controlled friction at the distal end of tubes 122 on the pull wires 44, sleeves 123 are received in holes in the distal face of distal frame member 94. Set screws 125 hold the sleeves 123 in place and can be used to increase friction by tightening. In this way, friction on the pull wires 44 can be adjusted to permit axial motion of the wires while the handle is being shaped, while holding the wires in place when the handle is not being shaped.

Referring now to FIGS. 12–16, a further embodiment of shapable handle 24 of the present invention will be described. In this embodiment, shapable handle 24 will include, as in previous embodiments, a nose cover 92 to which shaft 10 is attached, a deformable body 28, preferably comprising convoluted tubing 104, and a proximal frame member 106 to which electrical connector 32 is mounted. Convoluted tubing 104 has a pair of axial passages 150 disposed longitudinally through its sidewalls on opposing lateral sides thereof. Pull wires 44 extend from shaft 10 through a pair of axially disposed passages 152 in nose cover 92 and through axial passages 150 in convoluted tubing 104. Pull wires 44 are secured at their proximal ends to retaining screws 154 in proximal frame member 106. Preferably, a pair of hypotubes 156 of a rigid material such as stainless steel are secured to proximal frame member 106 and extend distally from retaining screws 154 into axial passages 150 near the proximal end of convoluted tubing 104. Pull wires 44 extend through the hypotubes for attachment to retaining screws 154. Proximal frame member 106 is secured to convoluted tubing 104 by means of a crimp ring 158.

FIGS. 12 and 13 illustrate an alternative means of coupling core wire 42 to torquer ring 96. In this embodiment, inner ring 100 comprises a pinion gear 103 secured to the proximal end of core wire 42. Pinion gear 103 includes a plurality of gear teeth 160 configured to engage drive teeth 162 of complementary configuration on the inner surface of torquer ring 96. In this way, rotation of torquer ring 96 will exert torque on the proximal end of core wire 42 so as to rotate the distal tip of catheter shaft 10, as described above. The relative diameters and number of teeth of pinion gear 103 and torquer ring 96 will be selected to provide the desired ratio of torquer ring rotation to core wire rotation, usually between 1:1.5 and 1:8, and preferably about 1:4.

FIGS. 12 and 14 illustrate a further preferred embodiment of handle 24 in which a spine 163 is disposed in central bore 112 for maintaining the shapable handle in a deflected shape. Spine 163 comprises a plurality of linked elements 164. Linked elements 164 are pivotally mounted to one another so as to pivot about at least one axis generally transverse to the axial direction (defined by shaft 10). In a preferred embodiment, linked elements 164 comprise, as illustrated in FIG. 16, a ball portion 166 at a distal end, and a socket portion 168 at a proximal end. Socket portion 168 is configured to receive the ball portion 166 of the adjacent linked element 164. A rim 170 about the proximal end of socket portion 168 provides a snap fit of ball 166 into socket 168. In this way, elements 164 are pivotable about 360° relative to one another. A bore 172 at the distal end of each element 164 provides an axial passage through spine 113 for receiving thermocouple wires 48 and electrode wires 46, which extend through the spine and attach at their proximal ends to electrical connector 32. Linked elements 164 may be a rigid polymer such as polyimide, polyetherimide, polycarbonate, or ABS, or biocompatible metal such as stainless steel. Spine 163 is secured at its proximal end to a ball extension 174 on proximal frame member 106. Ball extension 174 is configured like ball portions 166 of linked elements 164, so as to snap into socket portion 168 of the proximal-most linked element. Similarly, the proximal end of nose cover 92 has a socket 176 which receives the ball portion 166 of the distal-most linked element 164. In this way, spine 163 provides hoop strength and axial reinforcement for convoluted tubing 104, while facilitating lateral deflection of shapable handle 24 in any lateral direction desired. In addition, the frictional engagement of linked elements 164 with each other retains handle 24 in a deflected shape, holding at least one of pull wires 44 in tension so as to maintain the distal tip of the catheter in a deflected configuration.

In other respects, the shapable handle of FIGS. 12-16 is similar to that described above with reference to FIG. 9. It should be understood that linked elements 164 comprising reinforcing means 113, or pinion gear 103 coupling core wire 42 to torquer ring 96, may be used in place of spring 113 or knurled ring 100 of FIG. 9. Similarly, the knurled ring 100 of FIG. 9 may be used in place of pinion gear 103 in FIG. 12 for coupling core wire 42 to torquer ring 96.

Figure 10:
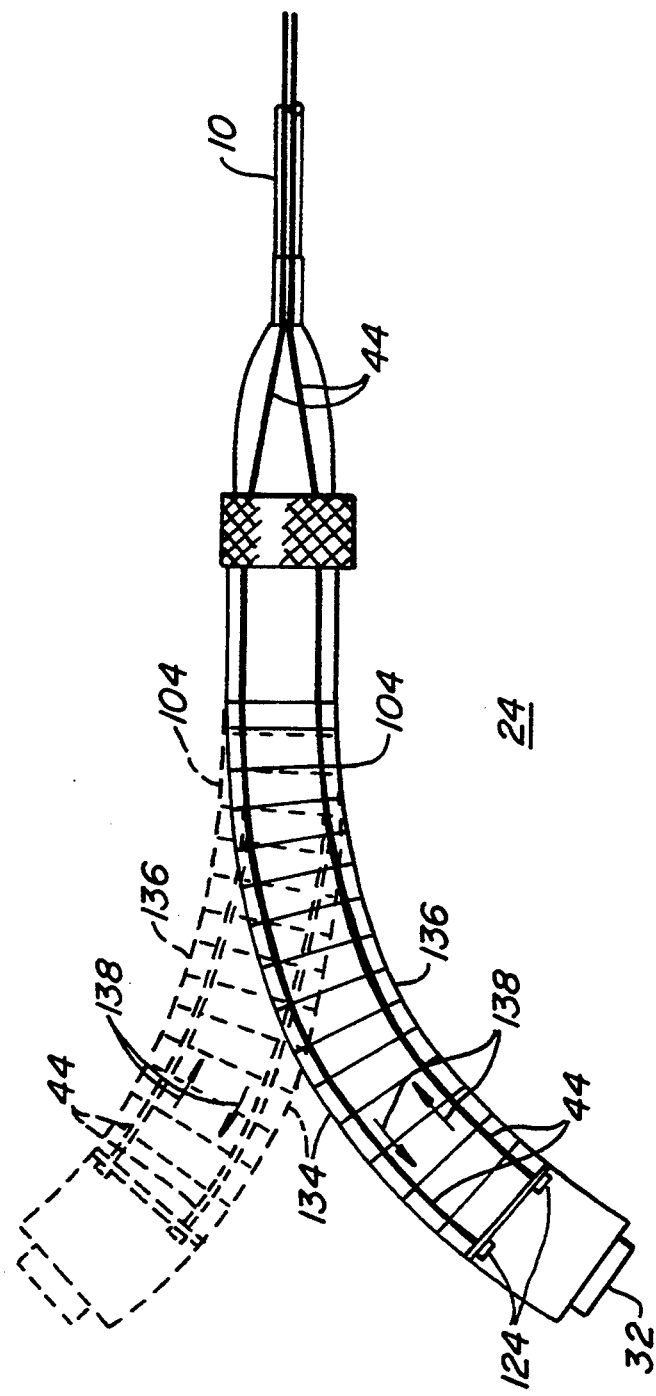
FIG. 10 is a schematic illustrating deformation of the shapable handle of the catheter of FIG. 1.

Referring now to FIG. 10, convoluted tubing 104 is preferably nylon or other flexible material, and is configured to have alternating cylindrical segments of larger and smaller diameter such that the tubing is longitudinally expandable and contractible. This permits the convoluted tubing member 104 to be deflected laterally with respect to a distal portion. By such deflection, a lateral portion 134 of tubing member 104 at the outside of the bend becomes elongated, while the opposing lateral portion 136 at the inside of the bend is shortened. In this manner, pull wires 44 in tubes 122 are subject to tension or relaxation, depending upon in which lateral portion of tubing member 104 they are disposed, as shown by arrows 138.

Materials and dimensions of the convoluted tubing 104 or other deformable member comprising body 28 are selected so as to provide sufficient flexibility for deflection, and to be "deformable," i.e., to be substantially nonresilient so as to remain in a deflected position when force is released from the handle. Convoluted tubing 104 may alternatively comprise a plurality of alternating disks of larger and smaller diameter on a bendable core of a soft, malleable material such as copper or brass.

With this construction, as shown in FIG. 10, lateral deflection of a proximal portion of handle 24 by bending convoluted tubing member 104 exerts a tensile force to the pull wires 44 at the outside portion 134 of the bend, while relaxing tension to pull wires at the inside portion 136 of the bend. Accordingly, at the distal end of the catheter, pull wires 44 brought into tension pull the distal end via anchor plate 72, with the opposing relaxed pull wires allowing the tube to deflect. The attachment of pull wires 44 to handle 24 may be configured so that a particular deflection of handle 24 produces deflection of distal tip of the catheter in a desired direction, either corresponding to or complementary to the direction of deflection of handle 24.

The amount of radial offset of the points of attachment of pull wires 44 at the distal end of the catheter shaft relative to the radial offset of the offset passages in the shapable handle may be adjusted so that a given deflection in handle 24 will produce a desired degree of deflection of distal tip section 16. Preferably, the radial offset of the offset passages in handle 24 will be substantially greater than that of pull wires 44 in tip section 16. In an exemplary embodiment, offset passages 150 (FIG. 12) will be 5 mm-30 mm, preferably about 1 cm, from the axial centerline of handle 24, while lumens 43 (FIG. 5) in tip section 16 will be about 0.2 mm to 8 mm, preferably about 0.5 mm from the axial centerline of shaft 10. Further, the length of handle 24 and/or offset passages 150 may be selected so as to produce a desired degree of deflection of tip section 16 for a given deflection of handle 24. The handle will usually be between 1 cm and 20 cm in length, and preferably about 10 cm in length.

Figure 11:
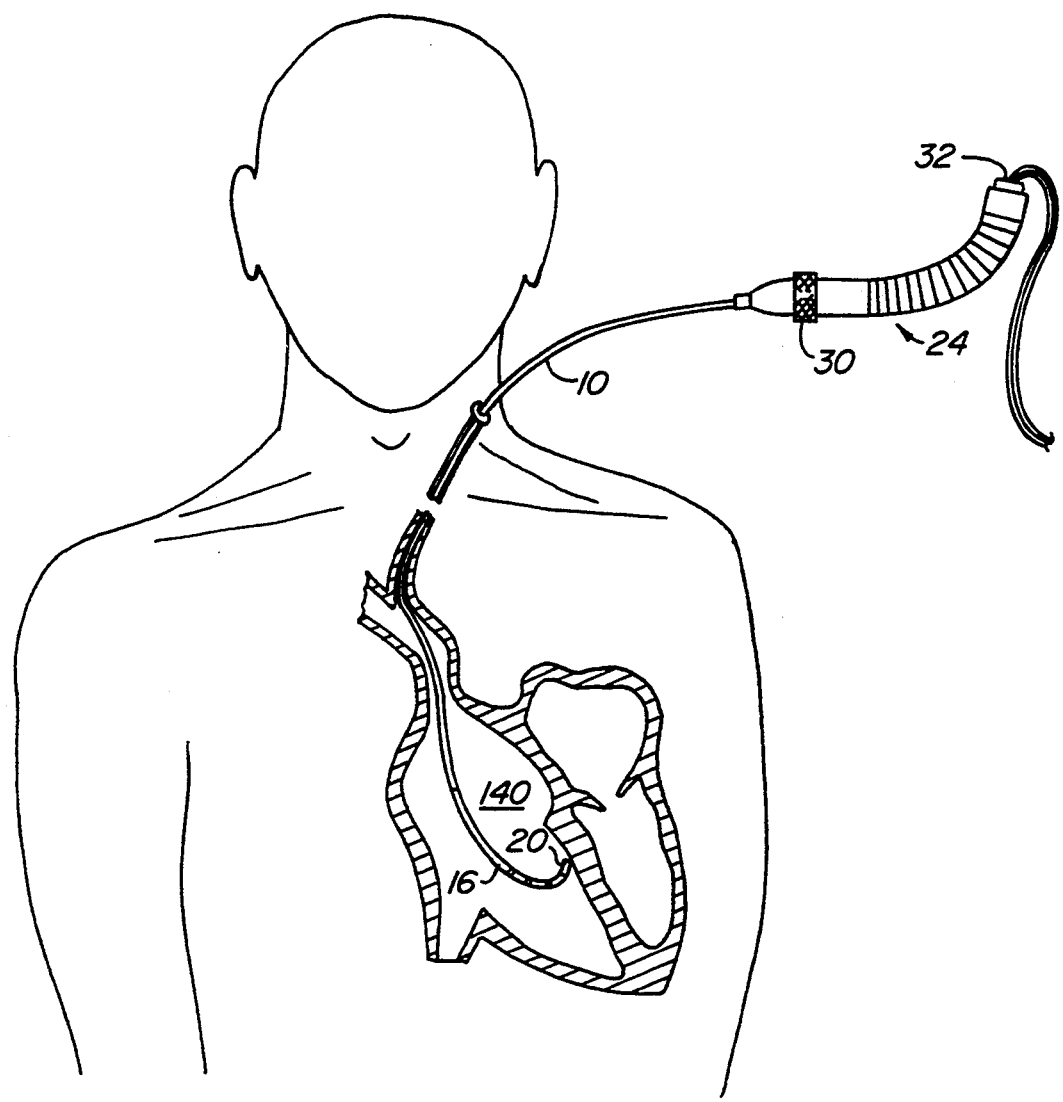
FIG. 11 is a schematic of the catheter of FIG. 1 positioned in the heart of a patient according to the principles of the present invention.

Using the handle and catheter of the present invention, an electrode 20 is positioned within a chamber of the heart using the catheter shown in FIGS. 1-9. As illustrated in FIG. 11, the electrode 20, disposed at the distal end of the catheter 8 as described above, is percutaneously introduced through a major vein or artery, such as the aorta, to the heart chamber 140. Electrode 20 may then be positioned near the target site on the interior wall of the heart chamber for ablation. This is accomplished by deflecting shapable handle 24 so as to produce a corresponding deflection in distal tip section 16. Further rough positioning can be achieved by rotating or twisting handle 24 such that the entire catheter assembly rotates, translating the rotational motion to tip section 16. Fine positioning is then accomplished by rotating torquer ring 30 on handle 24, which turns core wire 42, applying a torque to tip section 16. This provides precise and controllable rotational positioning of tip electrode 20 at the target site. Ablation may then be performed by applying RF energy to the target location through electrode 20, which is coupled to connector 32 via wires 46, connector 32 being connected to an RF power supply.

While the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

What is claimed is:

1. A steerable catheter comprising:
   a catheter shaft having a distal end, a proximal end, and a lumen extending therebetween, wherein a distal portion of the shaft is laterally deflectable;
   at least two pull wires disposed in the lumen having distal ends attached to radially offset positions at the distal end of the catheter shaft and proximal ends opposite the distal ends;
   a deformable handle body having a distal end secured to the proximal end of the catheter shaft, a proximal end opposite the distal end and at least two radially offset passages disposed axially therebetween, the pull wires extending through the offset passages and attached at their proximal ends to the proximal end of the handle body, wherein laterally deflecting the handle body lengthens a first of the offset passages and shortens a second of the offset passages to deflect the distal portion of the shaft; and
   means in the handle body for maintaining the handle body in a laterally deflected shape.

2. The catheter of claim 1 wherein the deformable handle body includes an axially extending central passage, and wherein the shape maintaining means comprises a spine disposed in the central passage of the handle body having a plurality of linked elements pivotally coupled to one another.

3. The catheter of claim 2 wherein the linked elements each comprise a first end having a socket and a second end having a ball, the socket of one linked element receiving the ball of another linked element.

4. The catheter of claim 2 wherein the spine comprises at least three linked elements.

5. The catheter of claim 1 wherein the deformable handle body includes an axially extending central passage, and wherein the shape maintaining means comprises a coil spring disposed in the central passage of the handle body.

6. The catheter of claim 1 wherein the deformable handle body includes an axially extending central passage, and wherein the shape maintaining means comprises a deformable tube of soft metal disposed in the central passage of the handle body.

7. The catheter of claim 1 wherein the deformable handle body includes an axially extending central passage, and wherein the shape maintaining means comprises means disposed in the offset passages in the handle body, for frictionally engaging the pull wires to hold the pull wires in tension.

8. The catheter of claim 1 wherein the handle body comprises convoluted tubing.

9. The catheter of claim 1 further comprising means for torquing the deflectable portion of the shaft about a longitudinal axis without rotating the handle body.

10. The catheter of claim 9 wherein the means for torquing comprises a core wire disposed in the lumen of the catheter shaft having a distal end coupled to the deflectable portion of the shaft and a proximal end disposed in the handle body, and means mounted to the handle body for applying torque to the proximal end of the core wire.

11. The catheter of claim 10 wherein the means for applying torque comprises a torquer ring rotatably mounted to the handle body, and an inner ring rotatably mounted in the handle body and fixed to the proximal end of the core wire, the inner ring engaging an inner surface of the torquer ring so as to rotate therewith.

12. The catheter of claim 1 wherein the radially offset positions of the pull wires at the distal end of the catheter shaft are substantially closer to an axial centerline of the catheter shaft than the radially offset passages in the handle body are to an axial centerline of the handle body, whereby producing a first deflection in the handle body produces a substantially larger deflection in the distal portion of the shaft.

13. The catheter of claim 1 further comprising at least one electrode on the deflectable tip with lead wires extending proximally therefrom, and a connector mounted to the handle body and coupled to the lead wires for connecting to a radiofrequency generator.

14. A combination shapable handle assembly and steerable shaft comprising:
   the shaft having proximal and distal ends;
   a deflectable tip at the distal end;
   a linkage coupled to the deflectable tip disposed in an axial passage in the shaft;
   a deformable handle body having a distal end configured for attachment to the proximal end of the shaft, a proximal end opposite the distal end, and a central passage and at least one radially offset passage disposed axially therebetween, the linkage extending through the offset passage and a coupled to a proximal portion of the handle body, wherein laterally deflecting the handle body lengthens the offset passage to deflect the distal tip; and
   means in the handle body for maintaining the handle body in a laterally deflected shape.

15. The combination of claim 14 wherein the linkage comprises at least one pair of pull wires having distal ends coupled to radially offset locations of the deflectable tip and proximal ends attached to radially offset locations at the proximal end of the handle body, a first pull wire being disposed in a first offset passage in the handle body and a second pull wire being disposed in a second offset passage in the handle body, whereby laterally deforming the handle body tensions the first pull wire and relaxes the second pull wire.

16. The combination of claim 14 wherein the shape maintaining means comprises a spine disposed in the central passage of the handle body having a plurality of linked elements pivotally coupled to one another.

17. The combination of claim 16 wherein the linked elements each comprise a first end having a socket and a second end having a ball, the socket of one linked element receiving the ball of another linked element.

18. The combination of claim 16 wherein the spine comprises at least three linked elements.

19. The combination of claim 14 wherein the shape maintaining means comprises a coil spring disposed in the central passage of the handle body.

20. The combination of claim 14 wherein the shape maintaining means comprises a deformable tube of soft metal disposed in the central passage of the handle body.

21. The combination of claim 14 wherein the shape maintaining means comprises means disposed in the offset passage in the handle body for frictionally engaging the pull wire to hold the pull wire in tension.

22. The combination of claim 14 wherein the handle body comprises convoluted tubing.

23. The combination of claim 14 further comprising means for torquing the deflectable tip about a longitudinal axis without rotating the handle body.

24. The combination of claim 23 wherein the means for torquing comprises a core wire disposed in the axial passage of the shaft having a distal end coupled to the deflectable tip and a proximal end disposed in the handle body, and means mounted to the handle body for applying torque to the proximal end of the core wire.

25. The combination of claim 24 wherein the means for applying torque comprises a torquer ring rotatably mounted to the handle body, and means fixed to the proximal end of the core wire for engaging an inner surface of the torquer ring so as to rotate therewith.

26. The combination of claim 25 wherein the means for engaging the inner surface of the torquer ring comprises an inner ring having an outer surface for frictionally engaging the inner surface of the torquer ring.

27. The combination of claim 25 wherein the means for engaging comprises a pinion gear having a plurality of gear teeth, the torquer ring having a plurality of drive teeth on its inner surface for engaging the gear teeth.

28. The combination of claim 25 wherein the torquer ring and the means for engaging the inner surface of the torquer ring are configured to provide a ratio of torquer ring rotation to core wire rotation of at least about 1:1.5.

29. The combination of claim 15 wherein the radially offset locations of the pull wires at the distal end of the shaft are substantially closer to an axial centerline of the shaft than the radially offset passages in the handle body are to an axial centerline of the handle body, whereby producing a first deflection in the handle body produces a substantially larger deflection in the distal portion of the shaft.

30. The combination of claim 14 wherein the catheter further comprises at least one electrode on the deflectable tip with lead wires extending proximally therefrom, the shapable handle including a connector mounted to the handle body and coupled to the lead wires for connecting to a radiofrequency generator.

31. A steerable catheter comprising:
a catheter shaft having a distal end, a proximal end, and a central lumen extending therebetween, wherein a distal portion of the shaft is laterally deflectable;
a core wire disposed in the central lumen having a distal end secured to the distal end of the catheter shaft and a proximal end opposite the distal end;
at least one pull wire disposed in the central lumen having a distal end attached to a radially offset position at the distal end of the catheter shaft and a proximal end opposite the distal end;
a handle secured to the proximal end of the catheter shaft;
means on the handle for exerting tension on the pull wire to laterally deflect the distal portion of the catheter shaft; and
means coupled to the handle for torquing the core wire about a longitudinal axis without rotating the handle.

32. The catheter of claim 31 further comprising at least a first electrode disposed on the deflectable tip; lead wires coupled to the electrode and extending through the central lumen to the handle body; and a connector mounted to the handle and coupled to the lead wires for connecting to a radiofrequency power supply.

33. The catheter of claim 31 wherein the handle comprises a shapable handle body having a distal end secured to the proximal end of the catheter shaft, a proximal end opposite the distal end, and a central passage and at least one radially offset passages disposed axially therebetween, the pull wire extending through the offset passage and attached at its proximal end to the proximal end of the handle body, wherein shaping the handle in a laterally deflected shape tensions the pull wire to deflect the distal portion of the shaft.

34. The catheter of claim 33 further comprising means for maintaining the handle body in a laterally deflected shape.

35. The catheter of claim 34 wherein the maintaining means comprises a spine having a plurality of linked elements pivotally coupled to one another.

36. The catheter of claim 35 wherein the linked elements each comprise a first end having a socket and a second end having a ball, the socket of one linked element receiving the ball of another linked element.

37. The catheter of claim 35 wherein the spine comprises at least three linked elements.

38. The catheter of claim 33 wherein the handle body comprises convoluted tubing.

39. The catheter of claim 31 wherein the means for applying torque comprises a torquer ring rotatably mounted to the handle, and means fixed to the proximal end of the core wire for engaging an inner surface of the torquer ring so as to rotate therewith.

40. The catheter of claim 39 wherein the means for engaging the inner surface of the torquer ring comprises an inner ring having an outer surface for frictionally engaging the inner surface of the torquer ring.

41. The catheter of claim 39 wherein the means for engaging comprises a pinion gear having a plurality of gear teeth, the torquer ring having a plurality of drive teeth on its inner surface for engaging the gear teeth.

42. The catheter of claim 39 wherein the torquer ring and the means for engaging the inner surface of the torquer ring are configured to provide a ratio of torquer ring rotation to core wire rotation of at least about 1:1.5.

* * * * *